(12) United States Patent
Phillips et al.

(10) Patent No.: US 7,272,545 B2
(45) Date of Patent: Sep. 18, 2007

(54) METHOD AND APPARATUS FOR DESIGNING AND LOCATING CHEMICAL STRUCTURES

(75) Inventors: Christine J. Phillips, Slingerlands, NY (US); Sandra Velez, Ballston Spa, NY (US); Robert James Perry, Niskayuna, NY (US); Maia Alanna Navarrete, Saratoga Springs, NY (US)

(73) Assignee: General Electric Company, Schenectady, NY (US)

( * ) Notice: Subject to any disclaimer, the term of this patent is extended or adjusted under 35 U.S.C. 154(b) by 753 days.

(21) Appl. No.: 10/063,907

(22) Filed: May 22, 2002

(65) Prior Publication Data
US 2003/0220776 A1 Nov. 27, 2003

(51) Int. Cl.
*G06G 7/58* (2006.01)

(52) U.S. Cl. .............................. 703/12; 703/6; 703/11; 702/19; 702/27

(58) Field of Classification Search .................. 705/9, 705/22; 707/1, 3; 703/6, 12, 11; 702/19, 702/27
See application file for complete search history.

(56) References Cited

U.S. PATENT DOCUMENTS

| | | | | |
|---|---|---|---|---|
| 5,008,831 A * | 4/1991 | Feldman | ........................ | 703/12 |
| 5,265,030 A * | 11/1993 | Skolnick et al. | ............... | 703/11 |
| 5,555,366 A * | 9/1996 | Teig et al. | ................... | 711/169 |
| 5,572,439 A * | 11/1996 | Nishida et al. | ................ | 702/27 |
| 5,577,239 A * | 11/1996 | Moore et al. | ................... | 707/3 |
| 5,950,192 A * | 9/1999 | Moore et al. | ................... | 707/3 |
| 5,980,096 A * | 11/1999 | Thalhammer-Reyero | .... | 707/100 |
| 6,304,869 B1 * | 10/2001 | Moore et al. | ................... | 707/3 |
| 6,377,895 B1 * | 4/2002 | Horlbeck | ...................... | 702/22 |
| 6,654,736 B1 * | 11/2003 | Ellis et al. | ..................... | 707/3 |
| 6,708,120 B1 * | 3/2004 | Mayo et al. | ................... | 702/27 |
| 6,801,861 B2 * | 10/2004 | Mayo et al. | ................... | 702/27 |
| 6,804,611 B2 * | 10/2004 | Mayo et al. | ................... | 702/27 |
| 6,950,754 B2 * | 9/2005 | Mayo et al. | ................... | 702/19 |
| 6,983,227 B1 * | 1/2006 | Thalhammer-Reyero | ....... | 703/2 |
| 7,065,452 B1 * | 6/2006 | Armistead et al. | ............ | 702/27 |
| 7,199,809 B1 * | 4/2007 | Lacy et al. | .................. | 715/700 |
| 2001/0047398 A1* | 11/2001 | Rubenstein | ................. | 709/218 |
| 2002/0049625 A1* | 4/2002 | Kilambi et al. | ................ | 705/9 |
| 2002/0129004 A1* | 9/2002 | Bassett et al. | ................. | 707/1 |
| 2003/0097305 A1* | 5/2003 | Ogino et al. | .................. | 705/26 |

OTHER PUBLICATIONS

"Introducing Macromedia Flash 5", D. Cook, PC Support Advisor Update 150, pp. 9-12, May 2001.*

(Continued)

*Primary Examiner*—Fred Ferris
(74) *Attorney, Agent, or Firm*—Cantor Colburn LLP

(57) ABSTRACT

An exemplary embodiment of the invention relates to a method, system, apparatus, and storage medium for designing and locating chemical structures. The apparatus comprises a user accessible chemical design and query tool comprising a user interface including an interactive host and a database storing a graphical representation of at least one chemical design structure. Upon accessing the chemical design and query tool by a user, the user interface guides the user in selecting a chemical design structure, and submitting the chemical design structure to a provider system. The invention also includes a method, system, and storage medium.

24 Claims, 10 Drawing Sheets

OTHER PUBLICATIONS

"ADC/Chem Sketch", Version 5.0 Users Guide, Advanced Chemistry Development Inc., 2001.*

"Personal Experience with four kinds of Chemical Structure Drwaing Software", Li et al, Chem Inf. Comput. Sci. ACM 2004.*

"ACD/3D Viewer", Users Manual Version 5.0, Advanced Chemistry Development, 1994-2001.*

"Making a Sound in Chemical Information: The Importance of a Structure Editor in Information Retrieval", J. Currano, University of Illinois, ISSN 1083-5261, 1999.*

Chemical & Engineering News, "Web site makes debut for structure searches", Nov. 13, 1995.

www.molinspiration.com, "JME Molecular Editor".

* cited by examiner

FIG. 2

*Welcome to the ABC Co.*
*Chemical Wizard*

Find the fluid that you need
for your application. The flask host
will assist you in your search.

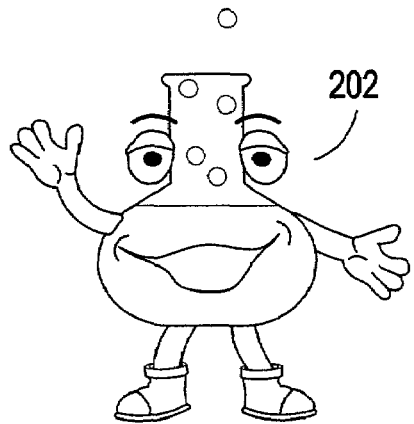

202

▷ Next

FIG. 3

*DISCLAIMER*

The flask host will ask you to draw a picture of the silicone
you need. There are many molecules that can be created
using the chemical wizard. In using this tool, you might possibly
draw molecules that have not yet been prepared or invented.
You should be aware that by submitting information,
you will be giving ABC Co., and its customers the right
to make, use, and sell any new molecules you may request.

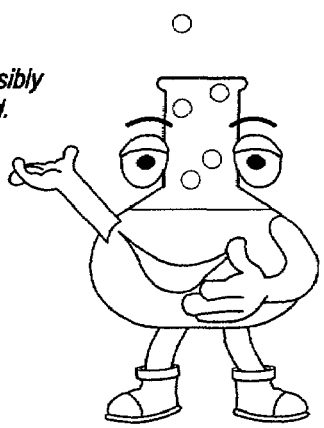

☒ I Disagree  ☑ I Agree

FIG. 6
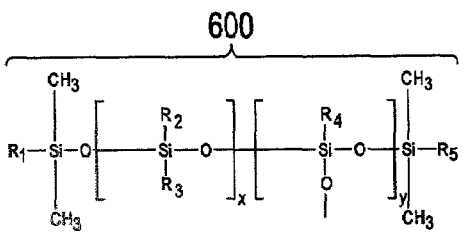
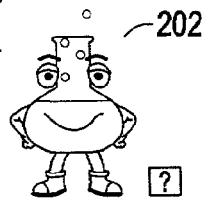
FIG. 7
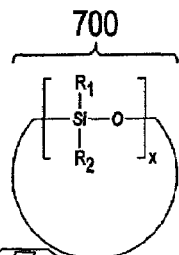
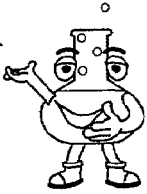

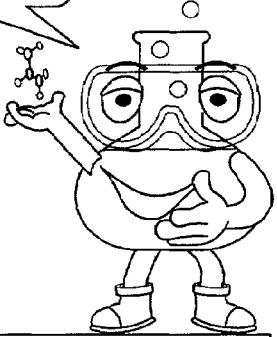

FIG. 16

```
                Chemistry Wizard WorkFlow Detail Screen
                This case is owned by XXXXXXX
       Customer #:            Case#:          Date Submitted:
       User information:              1602
1604   Name:               Address:
       State:              Zip Code:      Country:
       Tel:                eMail:

Wizard Data:
       Application:
       Contact Name:                e-Mail:
       Phone:                       Preferred Method of Contact:
1606   Backbone Type:
       R1:                          R4:
       R2:                          R5:
       R3:                          R6:

url to structure:
       Previous Comments:
       Comments:       Status: [ ↓ ]  Disposition:[ ↓ ]      All Comments

1608   [                                                              ]

E-mail to next reviewer: [ ↓ ]    Autoresponses:  [ ↓ ]

[ back ]   [ home ]   [ submit ]
```

- 1604: User information section
- 1602: Case# callout
- 1606: Wizard Data section
- 1608: Comments section

METHOD AND APPARATUS FOR DESIGNING AND LOCATING CHEMICAL STRUCTURES

BACKGROUND

The present invention relates to chemical design systems, and more particularly, to a computer-based method and system for designing, locating, and procuring polymers and chemicals.

Advancements in computer technology have led to an increase in electronic commerce (e-commerce) transactions for businesses and industries around the world. Business-to-business (B2B) tools for implementing these technologies are becoming increasingly important in today's competitive marketplace, due in part to economic influences and the evolving global economy.

For chemical vendors and manufacturers, this presents a special challenge. Specialty or custom chemical compounds are often difficult to describe or communicate in electronic form due to their extensive and sometimes convoluted nomenclature and diverse structural forms.

One solution developed to address this issue relates to an interactive web site for constructing and submitting molecules of interest. The solution allows a user to construct small organic molecules of interest with molecular modeling programs such as ChemDraw®, which utilizes a ChemDraw plug in, or the JME Molecular Editor©, which utilizes a Java Applet. This solution is cumbersome, as each individual bond, atom, and reactive group must be drawn by the user for each structure desired. The software also requires the user to have some knowledge of how to operate chemical drawing software. No known solutions exist, however, that allow for the construction of polymers of interest to the perspective customer. The need exists for a tool that can assist a user in selecting and functionalizing monomeric and polymeric materials and that is a convenient and easy to use method of placing related chemical inquiries.

BRIEF SUMMARY

An exemplary embodiment of the invention relates to a method, system, apparatus, and storage medium for designing and locating the chemical structure(s) for a particular chemical compound or polymer. The apparatus comprises a user accessible chemical design and query tool comprising a user interface that optionally includes an interactive host and a database storing a graphical representation of at least one chemical design structure. Upon accessing the chemical design and query tool by a user, the user interface guides the user in selecting a chemical design structure, and submitting the chemical design structure to a provider system. The invention also includes a method, system, and storage medium.

The above-described and other features and advantages of the invention will be appreciated and understood by those skilled in the art from the following detailed description, drawings, and appended claims.

BRIEF DESCRIPTION OF THE DRAWINGS

FIG. 2 illustrates a sample computer screen window including an interactive host that is presented to a user upon initiating the chemical wizard.

FIG. 3 illustrates a sample computer screen window displaying a disclaimer message.

FIG. 6 is a sample computer screen window illustrating a 'branched' backbone structure in an exemplary embodiment.

FIG. 7 is a sample computer screen window illustrating a 'cyclic' backbone structure in an exemplary embodiment.

FIG. 10 is a sample computer screen window including a subwindow listing chemistries available for a selected chemical substituent category, Amino.

FIG. 11 is a sample computer screen window illustrating a user-selected chemistry and instructions for guiding a user to add the chemical substituent to the selected backbone structure.

FIG. 12 is a sample computer screen window illustrating a backbone structure with an attached chemical substituent.

FIG. 13 is a sample computer screen and text window displaying user-provided comments and specifications. This screen is used to confirm that the information the user has provided is accurate before final submission of the requested chemical design structure to the provider system.

FIG. 14 is a sample computer screen window displaying contact information.

FIG. 15 is a sample computer screen response window including a link to information relating to a user's submitted inquiry.

FIG. 16 is a sample summary screen illustrating customer data and workflow details for tracking a product inquiry.

The words used to describe the figures are to be interpreted in terms of the definitions as used and defined herein and as defined by their use in context in this specification.

DETAILED DESCRIPTION

An exemplary embodiment of the invention is a network-based method and system that allows a user to construct the chemical structure of a molecule (chemical compound) or polymer of interest by choosing a backbone structure from a template palette and adding chemical substituents to the backbone from another set of templates. In the example of the chemical design and query tool (also referred to as the chemical wizard) described herein, the invention is used to construct an inorganic silicone monomer or polymer. The backbone palette offers the option of choosing between small molecule silanes, cyclic silicones or polymeric materials. A drag and drop feature reduces the time needed for constructing a molecule or polymer. A feature unique to the drag and drop method of drawing chemical structures employed by the present invention is that knowledge of chemical drawing software is not required. Another embodiment of the chemical wizard utilizes a drop down menu for selection of chemical substituents in addition to, or in place of, the drag and drop feature described above. Another embodiment of the chemical wizard utilizes a palette of graphical representations of chemical design structures, which can be selected by the user and submitted for search to the provider system. This method is used in place of or in addition to the method of utilizing separate palettes for chemical backbones and chemical substituents to construct the chemical design structure. In this application the word "design" when used in the phrase "chemical design structure" tends to have the meaning of a queried or sought chemical structure, compound, molecule, polymer or copolymer.

Figure 1:
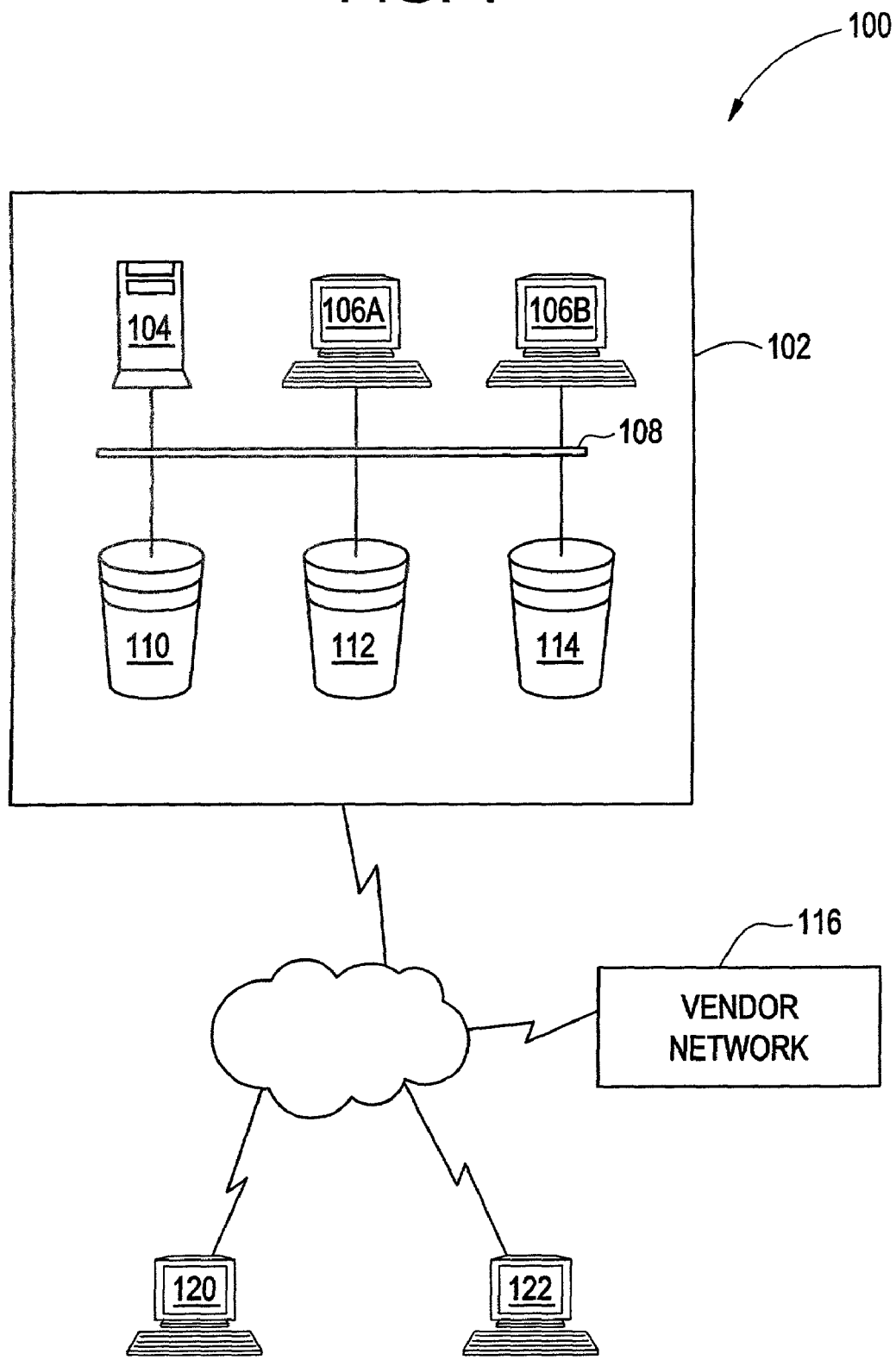
FIG. 1 illustrates a block diagram of a system for use in implementing the chemical wizard in an exemplary embodiment.

FIG. 1 illustrates an exemplary embodiment of various system components utilized for implementing the chemical wizard. System 100 comprises a host system 102 comprising a server 104, computer processing devices 106A and 106B, all of which are connected to a communications link 108. Host system 102 may be a chemical manufacturer, dealer, application service provider, or similar entity. In a preferred embodiment, server 104 executes the chemical wizard as well as web server software, business applications software, communications software, and a graphics tool. Server 104 may be a mainframe computer or similar high-powered processor including an internal data storage device for warehousing data and/or applications utilized by the chemical wizard as will be described further herein. Applications software executing on server 104 includes a workflow tool, a payment processing tool, and other general business applications commonly used in a business environment. Communications software preferably includes an electronic mail tool and may also include a suitable workgroup application for facilitating communications and tracking of customer inquiries throughout host system 102. Graphics software may be a vector-graphic animation tool such as Flash™ or other suitable application.

Computer processing devices 106A and 106B may each comprise a general-purpose computer processor such as a desktop or laptop and are capable of communicating with server 104 via communications link 108. Typical users of computer processing devices 106A and 106B include gatekeeper personnel of host system 102 as well as technical support specialists, customer service, sales, product management, and administrative personnel. These are described further herein. It should be noted that any number of computer processing devices may be included in host system 102 and that only two are shown for purposes of illustration. Communications link 108 may be a communications cable, an Intranet network link or any suitable networking means.

Databases 110, 12, and 114 may be stored on server 104 in its internal storage or may be stored externally in a data storage location accessible to server 104. Further, any number of databases may be used to implement the features and functions of the chemical wizard and thus, the three databases shown are meant to be illustrative and not to be interpreted as limiting in scope. Chemical database 110 stores the palette of chemical backbone structures (chemical structures), chemical substituents for each backbone structure, and available chemistries (molecules, compounds, polymers, and copolymers) associated with each chemical substituent. These items are described further herein. Customer database 112 stores registration information relating to customer accounts, chemical inquiries and summaries, payment and accounting data, as well as general administrative information. Customer database 112 also stores designed molecules created by customers via user systems 120 and 122. Workflow database 114 stores tracking information relating to customer inquiries as well as automated responses and text used in the processing of customer inquiries and orders.

A vendor network system 16 is also provided in system 100 and represents one or more business enterprises that engage in business with host system 102. Vendor network system 116 may include chemical manufacturing and supplier entities that perform related services for host system 102 pursuant to a trade agreement or contract. Host system 102 may be in communication via any suitable networking infrastructure such as Internet, Extranet, virtual private network, etc. Further, host system 102 has access to databases relating to chemical products available from vendor network 116 via the networking infrastructure in place.

User systems 120 and 122 represent general-purpose computer processing devices including web browser software and ISP connections for communicating with host system 102. User systems 120 and 122 may be desktops, laptops, or other similar computer processing devices. Typical users of user systems 120 and 122 include existing or potential customers of host system 102 where host system 102 is a chemical manufacturer, broker, or dealer. Additionally, users of user systems 120 and 122 may be registered users of the chemical wizard where host system 102 is an application service provider.

The chemical wizard enables a user to select multiple, independent chemical substituents, also described herein as functional groups or functionalities, to place on the backbones, and provides an interactive host to assist in customer queries. The wizard also optionally includes an animation tool and automated customer feedback features based on the availability of the molecule in question. In addition, the chemical wizard allows users to connect to other web sites that contain literature related to their query. The animated host provides basic direction to the user on how to operate the software and additional help functions can be activated to prompt the animated host to provide more detailed instructions on how to operate the chemical wizard. The animated host has several poses and positions, programmed in Flash™ or other similar software, which guide the user through the software and signal the user if the screen has been static for extended periods of time. The interactive host may communicate with the user through the use of speech, text bubbles, animated movements, sound, changes in color and facial expression, and/or other means of communication.

The chemical wizard captures and stores the custom chemical design structures that are built and submitted by the user in both customer database 112 and workflow database 114. The workflow application serves as an administrative tool that allows information to be reviewed, enables automatic communications with the customer, and allows for submissions to be tracked, accessed and acted upon in a timely and measurable manner. The workflow application enables a gatekeeper, such as a technical support specialist, to review the customer inquiry and forward the inquiry to any additional team members necessary to identify a commercial product that may be of interest to the customer. Once a product has or has not been identified, the gatekeeper can select from a menu of pre-written communications to send to the customer in response to their product inquiry. The workflow application also provides the gatekeeper with an option to customize or modify the text of a pre-written communication. Examples of autoresponses are described further herein.

The chemical wizard uses a robust animation tool such as Flash™, making it an interactive tool that visually morphs chemical structures through either drag and drop, double click, dropdowns or other interface readily understandable to the user. This may be accomplished in various ways. For example, a conventional linear 'click thru' application may be utilized that allows the user to add or modify one step at a time using recognizable HTML select boxes and radio buttons. Using client-side technology, the data can be updated on reload.

Another method of accomplishing this is by using dynamic HTML, whereby the chemical wizard allows the user to select an animated molecule, click on the desired structural change and have it animated. Another option includes a three-dimensional visualization of the molecule. This information can be stored on the client side before the option to purchase or submit. Once the user submits, this information may be stored for the client when they return using cookies or other technology.

Other embodiments include features such as re-display of the molecule the customer created via the workflow tool, the use of a choice of interactive hosts, and the storage and re-display of the molecule for the customers to view at a later date. Additional embodiments also include a feature which allows the user to view a list of properties or structure/function relationships associated with the chemical substituents, chemical backbones, and/or custom chemical design structure the user selects while using the chemical design and query tool. As an example, when the user selects the linear silicone backbone, the user would view a list of properties or attributes associated with this backbone such as oxidation resistance, ozone resistance, and UV resistance. As the user browses through the list of chemical substituent categories and/or chemical substituents, the user would view additional properties or attributes that would be added to the custom chemical design structure if that substituent were attached. As an example, if any of the chemical substituents in the "Phenyl" category were added to the backbone the user would view the additional property of "temperature resistance" added to the list of properties displayed for their custom chemical design structure.

It will be understood that while the invention is described with respect to the chemical wizard executing on a server at host system 102, some of the features and functions described with respect to the tool can be implemented at a client system (e.g., user systems 120 and 122) in order to appreciate the advantages of the invention. Thus, the description provided herein is not to be taken as limiting in scope.

The following FIGS. 2-17 demonstrate features of the chemical design and query tool, ranging from the user interface to the workflow process that handles the customer inquiries.

FIG. 2 illustrates a welcome screen including an interactive host 202 (also referred to as flask host) that is displayed when a user first accesses the chemical wizard.

FIG. 3 illustrates a computer screen window including a disclaimer message directing a user to either accept or reject the terms of using the chemical wizard. The tool may prevent a user from further access to the program unless the user accepts the terms of use.

Figure 4:
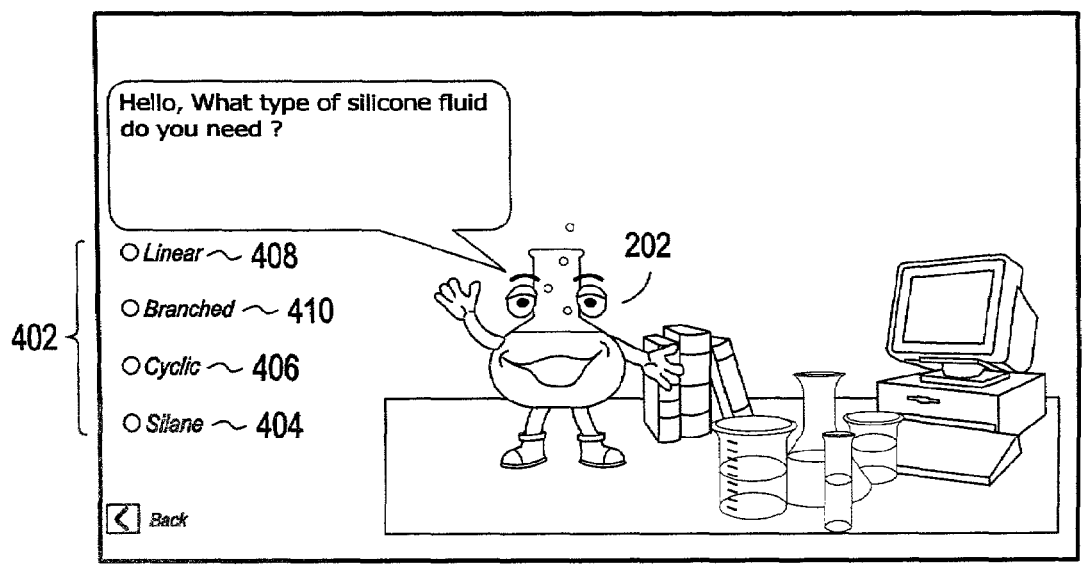
FIG. 4 illustrates a sample computer screen window for selecting a chemical backbone type from a palette of backbones. A selection of silicone backbones is shown in this example.

FIG. 4 illustrates a computer screen window whereby interactive host 202 prompts the user to select a type of chemical backbone that will serve as the basis for a product inquiry. A silicone backbone palette 402 is used in this example and offers the option for choosing between small molecule silanes 404, cyclic silicones 406, or polymeric materials such as linear silicones 408, or branched silicones 410.

Figure 5:
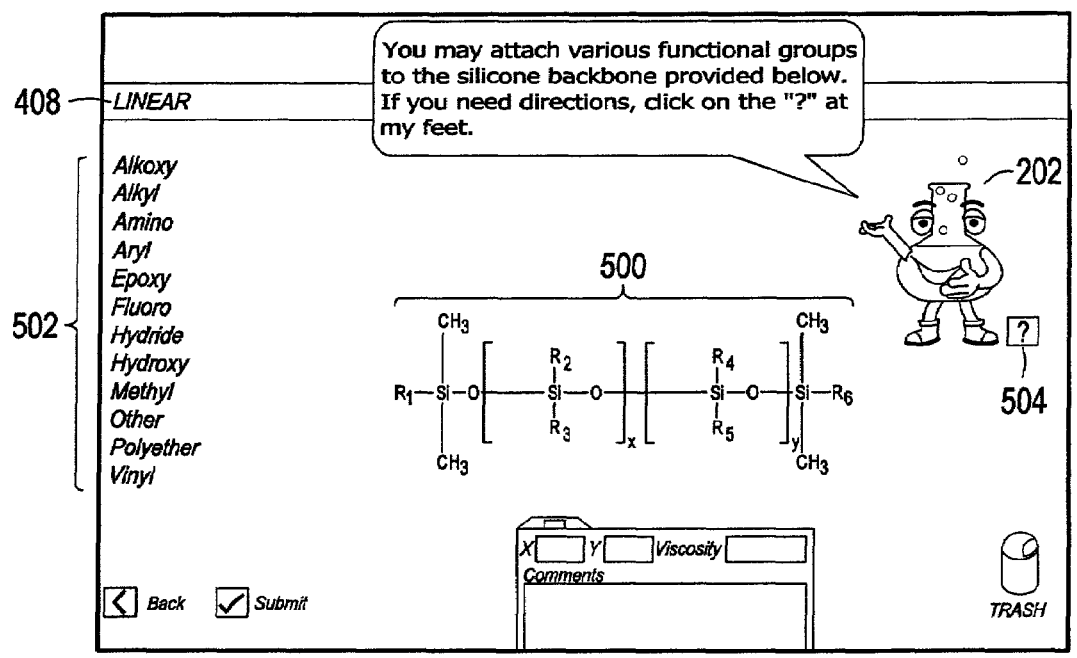
FIG. 5 is a sample computer screen window illustrating a 'linear' backbone structure in an exemplary embodiment.

FIG. 5 illustrates a computer screen window displayed to a user who has selected linear silicones 408 as a backbone. The chemical wizard accesses and retrieves a linear backbone structure 500 for display. Categories of chemical substituents 502 as shown in FIG. 5 include, but are not limited to, Alkoxy, Alkyl, Amino, Aryl, Epoxy, Fluoro, Hydride, Hydroxy, Methyl, Other, Polyether, and Vinyl. Interactive host 202 prompts the user to attach chemical substituents to the selected backbone. A 'help' feature is provided by the interactive host and may be accessed, in this example, by selecting the question mark symbol 504 near interactive host 202 to provide the user with step-by-step instructions on how to attach the chemical substituent to the backbone structure. FIG. 6 illustrates a computer screen window displayed to a user who has selected branched silicones 410. The chemical wizard accesses and retrieves a branched backbone structure 600 for display.

FIG. 7 illustrates a computer screen window displayed to a user who has selected cyclic silicones 406. The chemical wizard accesses and retrieves cyclic backbone structure 700 for display.

Figure 8:
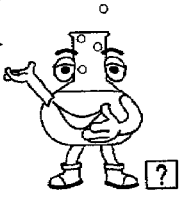
FIG. 8 is a sample computer screen window illustrating a 'silane' backbone structure in an exemplary embodiment.

FIG. 8 illustrates a computer screen window displayed to a user who has selected small molecule silanes 404. The chemical wizard accesses and retrieves silane backbone structure 800.

Figure 9:
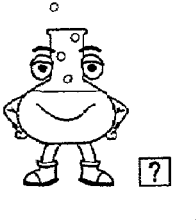
FIG. 9 is a sample computer screen window with instructions for guiding a user through a process of selecting a chemical substituent.

FIG. 9 illustrates a computer screen window with the help feature activated to guide the user through the process of selecting a chemical substituent category (also referred to as a chemical group) from which they will choose a chemical substituent to attach to their chemical backbone. The user is prompted to select a chemical substituent category from the group 502 displayed. A linear backbone structure 500 is illustrated.

Figures 10, 11:
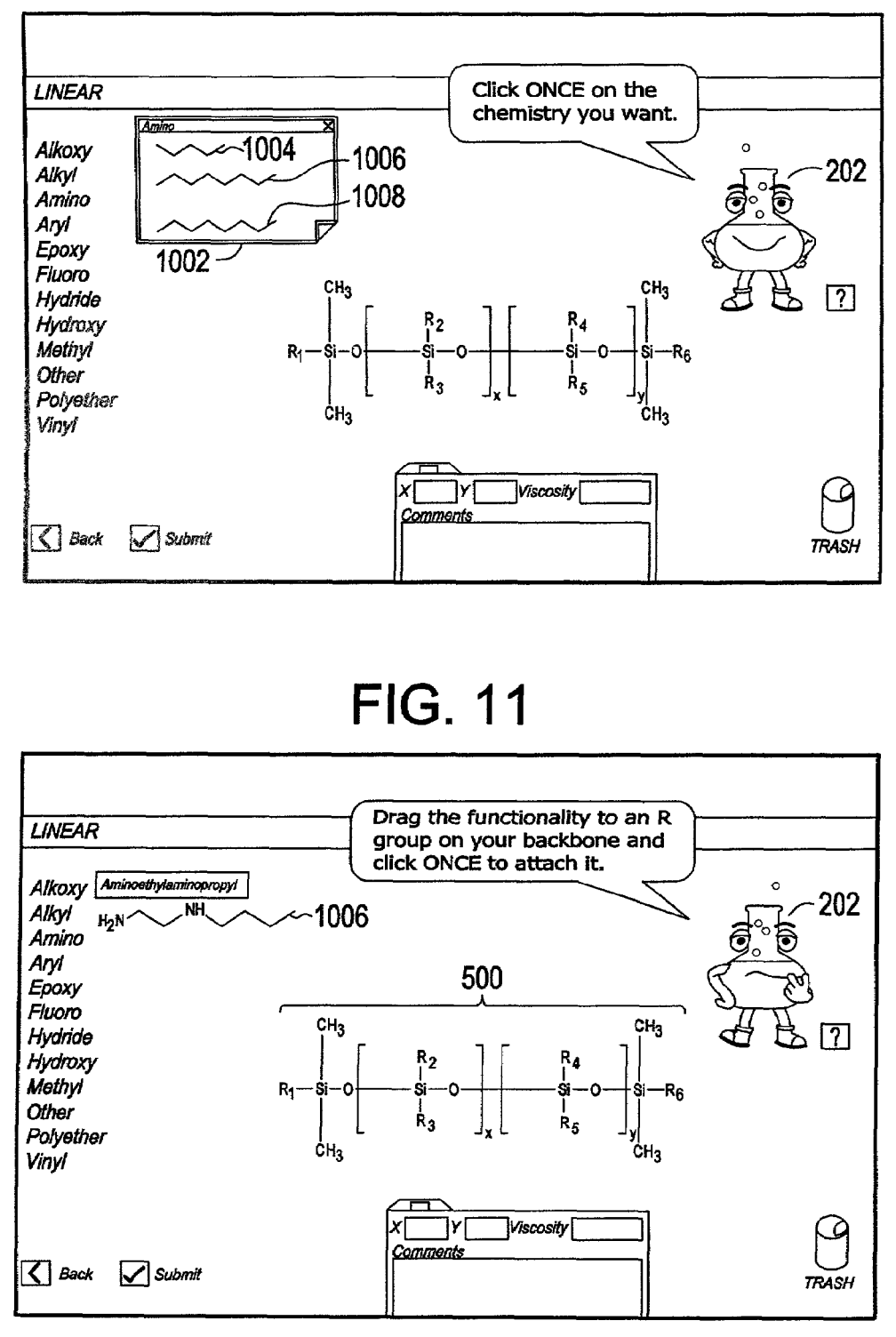

FIG. 10 illustrates a computer screen window and subwindow 1002 displaying available chemical substituents 1004, 1006, and 1008 for a selected chemical substituent category, Amino. With the help feature activated, the interactive host 202 provides instructions for selecting a chemical substituent from subwindow 1002. A chemical substituent category can include single or multiple selections of chemical substituents. A chemical substituent category and one of the substituents within the category can share the same name, for example a "Vinyl" chemical substituent category may offer a chemical substituent named vinyl. The name of the chemical substituent category may also be different than the chemical substituents grouped within it.

FIG. 11 illustrates a computer screen window including instructions from the help feature for attaching the selected chemical substituent 1006 to a desired location on the selected backbone structure 500. FIG. 11 indicates the selection of 'aminoethylaminopropyl' from the available chemistries provided in subwindow 1002. The user clicks on the chemical substituent 1006 and, using a 'drag' feature of the tool, moves the substituent 1006 to a desired "R" location on the selected backbone structure (in this example, linear backbone structure 500). An "R" group on the chemical backbone indicates a location where a chemical substituent may be attached. If a backbone contains multiple locations for attachment, the R groups are labeled as R1, R2, etc. Once the substituent is dragged over an R group, the R group will change color, or provide some visual and/or audio effect, indicating that it has been selected and the user can click a mouse or other suitable input device to attach the chemical substituent at that location.

Figures 12, 13:
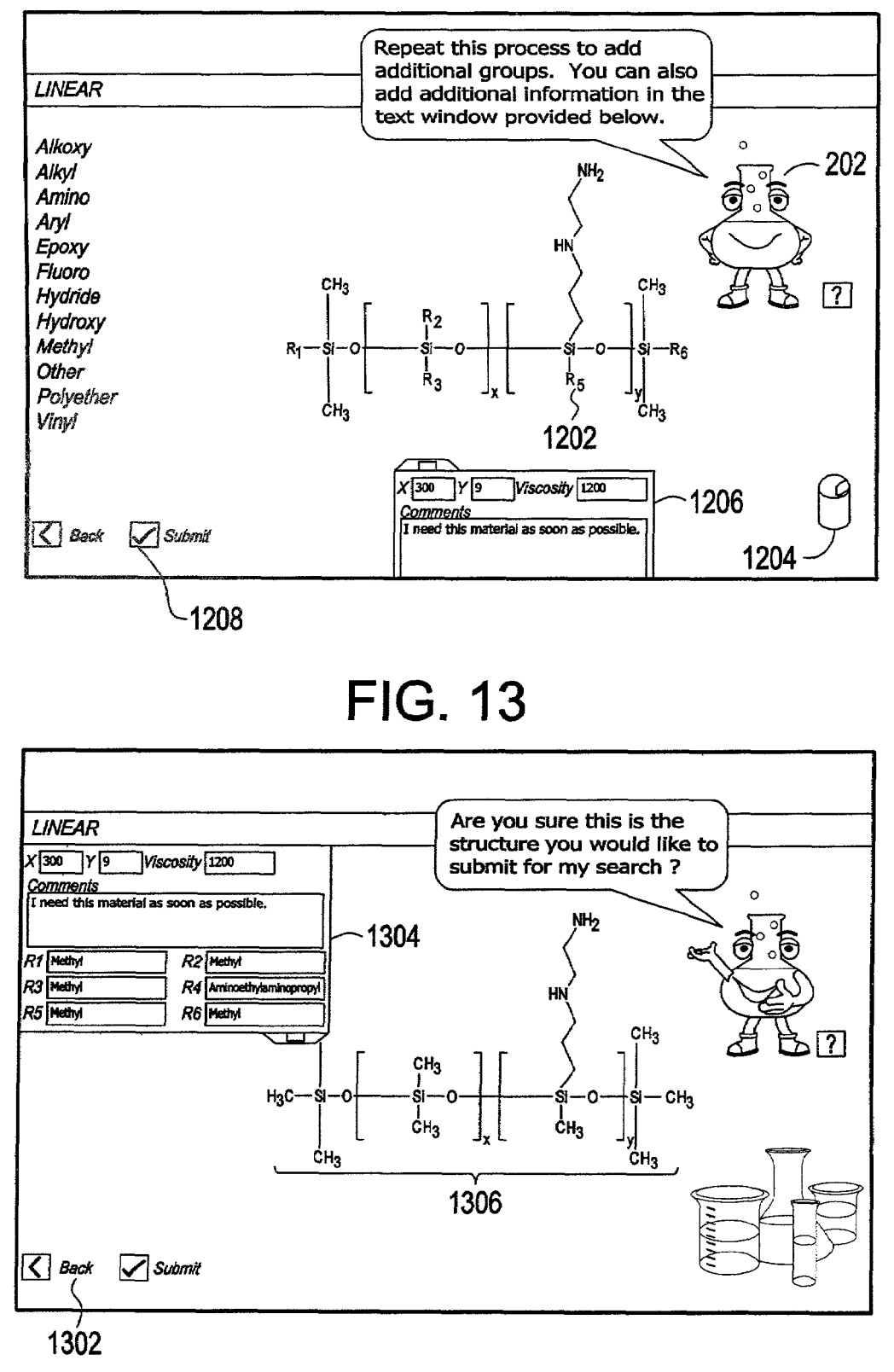

FIG. 12 illustrates a computer screen window whereby the user has selected the R4 location 1202 for attaching the chemical substituent 1006 to the backbone structure 500. At any time during the program, the user can discard a selected chemical substituent. This may be accomplished by dragging the substituent to the trashcan 1204 and clicking the mouse again to discard or by simply double clicking the mouse on the chemical substituent itself. Interactive host 202 guides the user with instructions, from the help feature, to repeat the process as desired for adding additional chemical substituents to the backbone and/or to provide additional information via a text window 1206. When the user has completed constructing their custom chemical design structure, the user submits their chemical design inquiry (also referred to as requested chemical design structure) by clicking on the 'submit' button 1208. The user is not required to assign a chemical substituent to all of the R groups located on the chemical backbone. In the event that the requested chemical design structure is submitted without a specified chemical substituent at an R group on the backbone structure, the chemical wizard can assign a default chemical substituent to those locations.

FIG. 13 illustrates a computer screen window in which interactive host 202 directs the user to confirm the information provided in previous computer screens. Additional edits may be made to the text window before submission or the user can select the 'back' button 1302 if they wish to edit any of the chemical substituents attached to the backbone. In this example, if an "R" group was not given a specific functionality, a methyl group ($CH_3$) is assigned to that position as a default as shown generally in subwindow 1304 and backbone structure 1306. It will be understood that other substituents may be selected as defaults by the tool where appropriate.

FIG. 14 illustrates a computer screen which requests information from the user relating to the application for which the information is being submitted as well as contact information.

FIG. 15 is a computer screen response window displaying a link 1502 to information on one or more web pages that relates to the chemical substituent(s) that was attached to the backbone. This link 1502 may be dynamic and can change with each search based on the groups the user selects while constructing a custom chemical design. In this example, the user is provided with a link to more information on amino functional fluids since this was the functionality of interest. The user may be contacted by email or by phone with the results of their inquiry or the response to the user's chemical inquiry may be immediately displayed on the computer screen. In a preferred embodiment, immediate automated responses to the product inquiry are not provided to the user based on the proprietary nature of this information. The information the customer submitted is preferably routed through a workflow transactional application and forwarded to the appropriate technical contact. The workflow transactional application supports processes to ensure tracking and response of individual requests.

Once the inquiry is submitted to customer database 112 and workflow database 114, the data is managed by a workflow application. A sample summary screen that would appear in the workflow application from the product inquiry provided in the example of FIGS. 2-15 is shown in FIG. 16. A case number 1602 is assigned to each product inquiry and the workflow application assigns ownership of the case to the gatekeeper, provided in customer database 112, who first views the inquiry submitted by a corresponding user of the chemical wizard. Section 1604 includes registration data for a customer. Section 1606 provides the specific contact information that the user provided with their product inquiry as well as information relating to the inquiry itself, such as application data, backbone type, selected chemical substituent data, and user comments. The selected chemical substituent data includes the name(s) of the chemical substituent(s) the user selected and the location(s) of attachment on the backbone structure. Section 1608 includes workflow and tracking information for assisting gatekeepers, technical specialists, and/or administrative personnel of host system 102 in processing the inquiry through to its final disposition.

Figure 17:
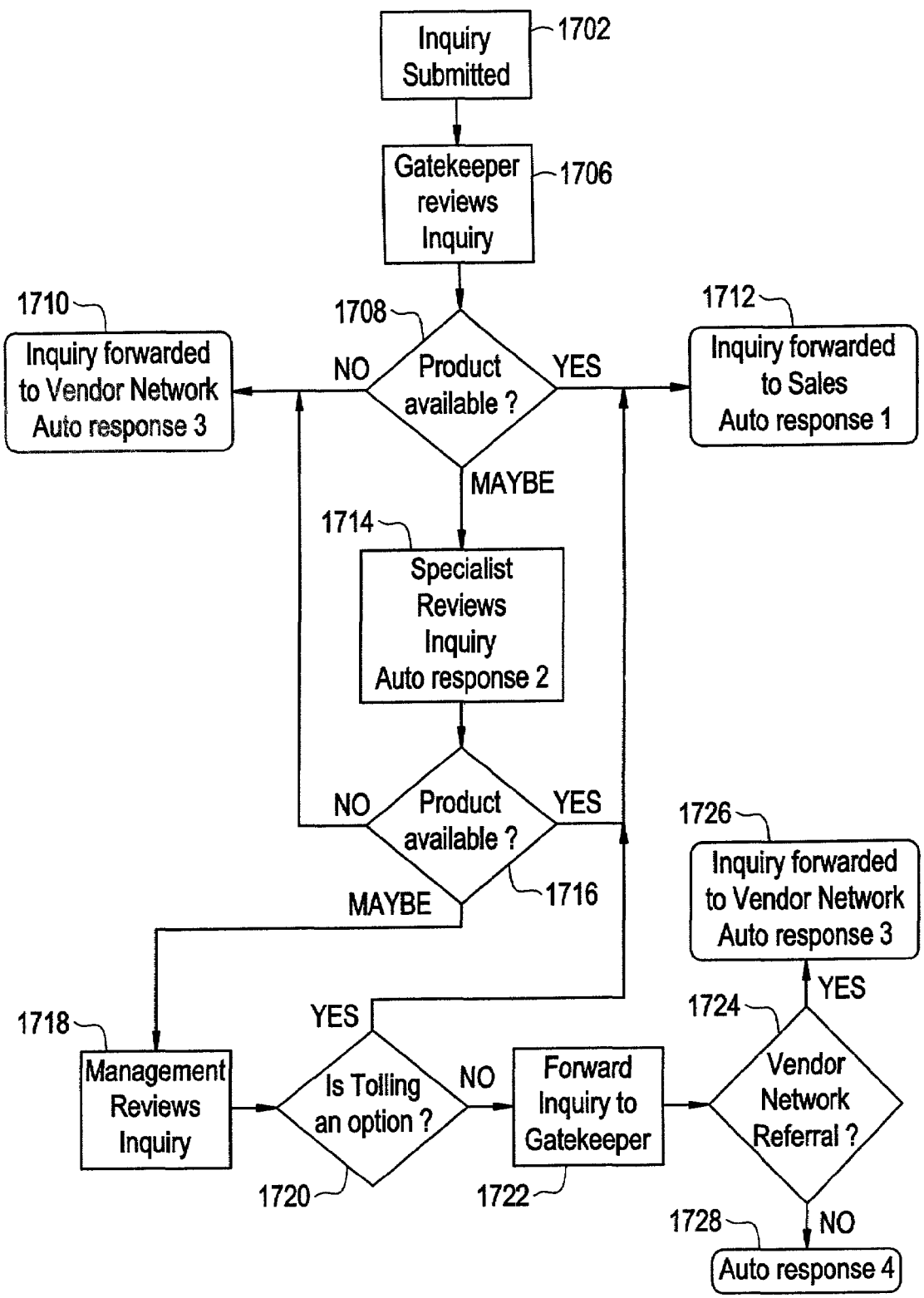
FIG. 17 is a flowchart describing how the chemical design and query tool processes a product inquiry in an exemplary embodiment.

FIG. 17 describes the process flow of information transmitted and processed by the workflow application. A user submits an inquiry at step 1702 utilizing the chemical wizard. The chemical wizard automatically routes the inquiry to a gatekeeper at one of computer processing devices 106A or 106B and/or to a central database where inquiries can be viewed. The gatekeeper represents the initial point of contact for a customer inquiry. The gatekeeper reviews the information in the inquiry at step 1706 and compares it against structures stored in chemical database 110, or other reference databases, at step 1708 in order to find a match. A second search of a vendor network database(s), or other system preferred by the vendor, may be performed at step 1708 as well. The gatekeeper function may be automated by the workflow application or may be a manual process. If the gatekeeper determines that a product match has been found in chemical database 110 or other suitable information database, the inquiry is forwarded to a person or department of interest, such as a sales department, and autoresponse 1 is transmitted to the customer at step 1712. A sample autoresponse 1 is provided below.

Autoresponse 1:

Thank you for using the ABC Co. chemical wizard. We have reviewed your inquiry and have determined that 'product x' is the product in our portfolio which most closely matches the chemical composition you requested. For more information about 'product x', please visit our website http://www.ABCco.com or contact a technical support representative at 800-123-4567. If you would like to submit another product search to the chemical wizard, please click <here>.

If no match is found in chemical database 110 but a potential match exists in a vendor network database or system, autoresponse 3 is transmitted to the customer along with an opportunity to indicate whether the customer would like to be referred to the vendor network at step 1710. A sample autoresponse 3 is provided below.

Autoresponse 3:

Thank you for using the ABC Co. chemical wizard. We have reviewed your inquiry and we do not currently offer a product in our portfolio that closely matches the chemical composition you requested. We have, however, identified a vendor in our vendor network that may sell the product you need. If you would like us to refer your product request to our vendor network, please click <here>. If you would like to submit another product search to the chemical wizard, please click <here>.

If the gatekeeper needs additional information in order to determine if a product match exists, the inquiry is forwarded to a specialist or consultant with ABC Co. at step 1714. At this time, autoresponse 2 is sent to the customer. A sample autoresponse 2 is provided below.

Autoresponse 2:

Thank you for using the ABC Co. chemical wizard. We have received your inquiry and we are reviewing our product portfolio to find a product that most closely matches the chemical composition you requested. You will receive notification by email with the final results of our search. If you need immediate assistance with your inquiry, please contact a technical support representative at 800-123-4567.

The product specialist performs a second review of the customer inquiry in order to determine product availability at step 1716. If a product match is found, the process reverts back to step 1712 whereby the inquiry is forwarded to a responsible person or department and autoresponse 1 is transmitted. If no product match is found in chemical database 110 but a match is found in a vendor network database, the process reverts to step 1710 whereby autoresponse 3 is transmitted to the customer with an opportunity to be contacted by the vendor network. The specialist can also forward the inquiry to a manager or specialist at step 1718 for further action. The manager may be part of a manufacturing or development group that is involved in producing new chemicals and/or fulfilling customer chemical orders. The management group considers whether manufacture of the subject chemical is an option. One factor in making this determination is whether tolling is an option at step 1720. If a customer does not have an urgent need for the chemical, manufacturing personnel may make arrangements with the customer to produce the product. In this manner, the process reverts to step 1712 as described above. If tolling is not an option for the customer, the inquiry is forwarded to the gatekeeper at step 1722 where it is decided whether a vendor network referral is feasible at step 1724. This may be an option where a vendor from the vendor network is able to produce the chemical on the customer's behalf. In this case, the inquiry is forwarded to the vendor network along with autoresponse 3 at step 1726. If this option is not feasible, then autoresponse 4 is transmitted to the customer. A sample autoresponse 4 is provided below.

Autoresponse 4:

Thank you for using the ABC Co. chemical wizard. We have reviewed your inquiry and we do not currently offer a product in our portfolio that closely matches the chemical composition you requested. For additional product needs, please visit our website at http://www.ABCco.com or contact a technical support representative at 800-123-4567. If you would like to submit another product search to the chemical wizard, please click <here>.

The description applying the above embodiments is merely illustrative. As described above, embodiments in the form of computer-implemented processes and apparatuses for practicing those processes may be included. Also included may be embodiments in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Also included may be embodiments in the form of computer program code, for example, whether stored in a storage medium, loaded into and/or executed by a computer, or as a data signal transmitted, whether a modulated carrier wave or not, over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed for carrying out this invention, but that the invention will include all embodiments falling within the scope of the appended claims. Further, persons possessing a baccalaureate degree or higher in chemistry are presumed to know how to write the formulae of chemical compounds as well as showing the structural and chemical relationships between the constituent atoms of a particular compound and this knowledge is subtended and presumed by the phrase "chemical design structure".

The invention claimed is:

1. A user accessible chemical design and query tool, comprising:
   a user interface;
   a database storing:
   a backbone menu including graphical representations for a plurality of chemical backbone structures each including at least one prespecified attachment point to which a user-selectable chemical substituent may be attached;
   each of the plurality of chemical backbone structures being associated with a corresponding substituent menu including a plurality of chemical substituents, any of which are user selectable for attachment to at least one prespecified attachment point of said chemical backbone structure such that, upon user selection of at least one chemical substituent from the substituent menu for attachment to at least one prespecified attachment point, a custom chemical design structure is specified;
   wherein, upon accessing said chemical design and query tool by a user, said user interface guides said user in performing at least one of:
   selecting the chemical design structure and submitting said chemical design structure to a provider system; and
   selecting the chemical backbone structure, attaching said graphical representation of said at least one chemical substituent to selected chemical backbone structure, and submitting a resulting custom chemical design structure to a provider system.

2. The user accessible chemical design and query tool of claim 1, further comprising:
   a text window operable for providing comments and further specifying said custom chemical design structure.

3. The chemical design and query tool of claim 1, further comprising:
   at least one R group included in said graphical representation of at least one chemical backbone structure, wherein said R group specifies an attachment point for attaching said at least one chemical substituent.

4. The chemical design and query tool of claim 1, further comprising an interactive host.

5. The chemical design and query tool of claim 1, wherein said at least one chemical substituent comprises at least one chemistry.

6. The chemical design and query tool of claim 1, wherein said chemical backbone structure is classified by at least one of:
   organic; and
   inorganic.

7. The chemical design and query tool of claim 4, wherein said interactive host guides said user in operating said tool.

8. The chemical design and query tool of claim 7, wherein said interactive host is animated, including a capability to take on a plurality of positions and poses.

9. The chemical design and query tool of claim 7, wherein said interactive host communicates with said user via at least one of:
- speech;
- sound;
- text bubbles;
- animated movements; and
- changes in color and facial expression.

10. The chemical design and query tool of claim 4, wherein a user selects said interactive host from a plurality of interactive host choices.

11. The chemical design and query tool of claim 3, wherein a chemical substituent is assigned to an R location by said tool as a default in the event that no chemical substituents were attached by said user.

12. The chemical design and query tool of claim 1, wherein said custom chemical design structure is created and edited utilizing interface techniques including at least one of:
- a linear click-thru application operable for allowing a user to add or modify a structure one step at a time using HTML select boxes;
- dynamic HTML technology operable for allowing a user to select an animated molecule, click on a desired structural change, resulting in a distinct structure; and
- a structure/function feature operable for:
- viewing properties associated with a backbone structure;
- viewing properties associated with a chemical substituent; and
- previewing additional properties that would be added to a backbone structure, if a specified substituent was attached to said backbone structure.

13. The chemical design and query tool of claim 1, wherein said chemical backbone structure includes a silicone backbone palette comprising:
- small molecule silanes;
- cyclic silicones; and
- polymeric materials including linear silicones and branched silicones.

14. A system for designing and locating chemical structures, comprising:
- a host system comprising:
- a server;
- a data storage device housing a customer database, a chemical database, and a workflow database, said data storage device accessible to said server;
- a chemical design and query tool executable by said server, said chemical design and query tool including a user interface for providing a backbone menu including graphical representations for a plurality of chemical backbone structures each including at least one prespecified attachment point to which a user-selectable chemical substituent may be attached;
- each of the plurality of chemical backbone structures being associated with a corresponding substituent menu including a plurality of chemical substituents, any of which are user selectable for attachment to at least one prespecified attachment point of said chemical backbone structure such that, upon user selection of at least one chemical substituent from the substituent menu for attachment to at least one prespecified attachment point, a custom chemical design structure is specified;
- a workflow component; and
- a link to at least one user system;
- wherein said host system tracks queries resulting from a custom chemical design structure created and submitted by user systems via said chemical design and query tool, and searches said chemical database for a compatible chemical structure and, depending upon search results, provides an autoresponse message to said user systems and performs related tracking activities via said workflow component.

15. The system of claim 14, further comprising a link to a vendor network system, said link operable for facilitating communication between said user system and at least one entity of said vendor network system, wherein said host system provides a link to a URL for said vendor network system upon finding a potential match to said queries.

16. The system of claim 14, wherein said workflow component includes a summary screen operable for facilitating tracking activities of queries, said summary screen comprising at least one of:
- a case number assigned to each query;
- an assignment of said query to a designated entity or individual;
- customer registration data;
- customer contact data;
- query data including:
- application data;
- backbone type;
- R group data; and
- user comments; and
- workflow and tracking information operable for assisting technical specialists, administrative personnel and gatekeepers of said host system in processing said query.

17. A method for designing and locating chemicals via a chemical design and query tool, comprising:
- receiving a welcome screen upon accessing said chemical design and query tool;
- providing a backbone menu including graphical representations for a plurality of chemical backbone structures each including at least one prespecified attachment point to which a user-selectable chemical substituent may be attached;
- each of the plurality of chemical backbone structures being associated with a corresponding substituent menu including a plurality of chemical substituents, any of which are user selectable for attachment to at least one prespecified attachment point of said chemical backbone structure such that, upon user selection of at least one chemical substituent from the substituent menu for attachment to at least one prespecified attachment point, a custom chemical design is specified; and
- submitting a resulting custom chemical design query to a host system.

18. The method of claim 17, further comprising an interactive host, said interactive host prompting a user through designing a custom chemical design structure.

19. A method for designing and locating chemicals via a chemical design and query tool, comprising:
- receiving a welcome screen upon accessing said chemical design and query tool;
- utilizing a drag and drop software routine for providing a backbone menu including graphical representations for a plurality of chemical backbone structures each including at least one prespecified attachment point to which a user-selectable chemical substituent may be attached; each of the plurality of chemical backbone structures being associated with a corresponding substituent menu including a plurality of chemical substituents, any of which are user selectable for attachment to at least one prespecified attachment point of said chemical backbone structure such that, upon user selection of at least one chemical substituent from the substituent menu for attachment to at least one prespecified attachment point, a custom chemical design is specified; and submitting a resulting custom chemical design query to a host system.

20. A method for designing and locating chemicals via a chemical design and query tool, comprising:

receiving a welcome screen upon accessing said chemical design and query tool;

utilizing a drop down software routine for providing a backbone menu including graphical representations for a plurality of chemical backbone structures each including at least one prespecified attachment point to which a user-selectable chemical substituent may be attached; each of the plurality of chemical backbone structures being associated with a corresponding substituent menu including a plurality of chemical substituents, any of which are user selectable for attachment to at least one prespecified attachment point of said chemical backbone structure such that, upon user selection of at least one chemical substituent from the substituent menu for attachment to at least one prespecified attachment point, a custom chemical design is specified; and submitting a resulting custom chemical design query to a host system.

21. A method for tracking custom chemical design queries, comprising:

receiving a custom chemical design query from a user system for providing a backbone menu including graphical representations for a plurality of chemical backbone structures each including at least one prespecified attachment point to which a user-selectable chemical substituent may be attached; each of the plurality of chemical backbone structures being associated with a corresponding substituent menu including a plurality of chemical substituents, any of which are user selectable for attachment to at least one prespecified attachment point of said chemical backbone structure such that, upon user selection of at least one chemical substituent from the substituent menu for attachment to at least one prespecified attachment point, the custom chemical design query is specified;

routing said custom chemical design query to a gatekeeper at a computer processing device or central storage location, said gatekeeper representing an initial point of contact for said query;

comparing data in said query with existing chemical structures;

if a match is found, transmitting a first autoresponse message to said user system;

if no match is found, comparing said query with structures available in a vendor network system;

if a match is found in said vendor network system, transmitting a second autoresponse message to said user system;

if no match is found in said vendor network system, determining whether tolling is an option;

if tolling is an option, transmitting a third autoresponse message to said user system; otherwise, transmitting a fourth autoresponse message to said user system.

22. A storage medium encoded with machine readable computer program code for designing and locating chemicals via a chemical design and query tool, said storage medium including instructions for causing said tool to implement a method comprising:

receiving a welcome screen including an interactive host upon accessing said chemical design and query tool;

providing a backbone menu including graphical representations for a plurality of chemical backbone structures each including at least one prespecified attachment point to which a user-selectable chemical substituent may be attached; each of the plurality of chemical backbone structures being associated with a corresponding substituent menu including a plurality of chemical substituents, any of which are user selectable for attachment to at least one prespecified attachment point of said chemical backbone structure such that, upon user selection of at least one chemical substituent from the substituent menu for attachment to at least one prespecified attachment point, a query for a custom chemical design structure is specified; and submitting the query to a host system.

23. The storage medium of claim 22, further comprising instructions for causing said computer to implement:

prompting a user through designing a custom chemical design structure utilizing an interactive host.

24. A storage medium encoded with machine-readable computer program code for tracking custom chemical design queries, said storage medium including instructions for causing said computer to implement a method comprising:

receiving a custom chemical design query from a user system, wherein said query is formulated by providing a backbone menu including graphical representations for a plurality of chemical backbone structures each including at least one prespecified attachment point to which a user-selectable chemical substituent may be attached; each of the plurality of chemical backbone structures being associated with a corresponding substituent menu including a plurality of chemical substituents, any of which are user selectable for attachment to at least one prespecified attachment point of said chemical backbone structure such that, upon user selection of at least one chemical substituent from the substituent menu for attachment to at least one prespecified attachment point, the query is formulated;

routing said query to a gatekeeper at a computer processing device or central storage location, said gatekeeper representing an initial point of contact for said query;

comparing data in said query with existing chemical structures;

if a match is found, transmitting a first autoresponse message to said user system;

if no match is found, comparing said query with structures available in a vendor network system;

if a match is found in said vendor network system, transmitting a second autoresponse message to said user system;

if no match is found in said vendor network system, determining whether tolling is an option;

if tolling is an option, transmitting a third autoresponse message to said user system;

otherwise, transmitting a fourth autoresponse message to said user system.

* * * * *